United States Patent [19]

Brodén

[11] Patent Number: 4,972,843
[45] Date of Patent: Nov. 27, 1990

[54] SAMPLE TAKING EQUIPMENT

[76] Inventor: Bengt-Inge Brodén, Gårdfarivägen 3, S-532 00 Skara, Sweden

[21] Appl. No.: 381,701
[22] PCT Filed: Jan. 12, 1988
[86] PCT No.: PCT/SE88/00002
§ 371 Date: Jul. 10, 1989
§ 102(e) Date: Jul. 10, 1989
[87] PCT Pub. No.: WO88/05286
PCT Pub. Date: Jul. 28, 1988

[30] Foreign Application Priority Data

Jan. 14, 1987 [SE] Sweden .................................. 8700109

[51] Int. Cl.$^5$ .............................................. A61B 5/00
[52] U.S. Cl. ..................... 128/760; 128/763; 128/764; 604/192
[58] Field of Search ..................... 128/760–766; 604/192, 197, 236, 263, 403, 411–413

[56] References Cited

U.S. PATENT DOCUMENTS

| 4,326,541 | 4/1982 | Eckels | 128/764 X |
| 4,409,991 | 10/1983 | Eldridge | 128/266 |
| 4,418,703 | 12/1983 | Hoch et al. | 128/763 X |
| 4,592,744 | 6/1986 | Jagger et al. | 604/192 |
| 4,731,059 | 3/1989 | Wanderer et al. | 128/764 X |
| 4,791,938 | 12/1988 | Van Valkenburg | 128/763 |
| 4,841,985 | 6/1989 | Wanamaker | 128/763 |
| 4,850,734 | 7/1989 | Diaz-Ramos | 128/763 |
| 4,886,072 | 12/1989 | Percarpio et al. | 128/763 |

Primary Examiner—Robert A. Hafer
Assistant Examiner—Kerry Owens
Attorney, Agent, or Firm—Sughrue, Mion, Zinn, Macpeak and Seas

[57] ABSTRACT

Equipment suited for taking fluid samples from patients includes a sample taking device which is provided with a front needle (2) and a rear needle (3) whose pointed ends face away from one another. The pointed end of the front needle (2) is intended for piercing a vein or like blood vessel, while the pointed end of the rear needle (3) is intended for piercing a sealing stopper of a vacuum-type test tube capable of being partially inserted into the sampling device. Defined between the mutually facing ends of respective needles is a space (9) which accommodates a flow regulator (10) for regulating the flow through the needles. The sample taking equipment is characterized in that it also includes a protective casing which is intended to accommodate the simple taking device and which includes a cover part (22) which protects the front needle point and a cover part (20) which co-acts with the flow regulator (10) in a manner such as to hold the flow passage through the needles (2,3) open when the sample taking device is introduced into the protective cover.

10 Claims, 2 Drawing Sheets

SAMPLE TAKING EQUIPMENT

The present invention relates to equipment suited for taking fluid samples from patients. The equipment includes a fluid sampling device which comprises front and rear needles which face away from one another and with which the pointed end of the front needle is configured for insertion into a blood vessel of a patient and the pointed end of the rear needle is configured for insertion into a sealing stopper located in a vacuum-type test tube which is capable of being inserted partially into the sampling device, and which sampling device incorporates in the space between the mutually opposing ends of the two needles a flow regulating valve means which is operative to regulate the flow of sample through the needles, said flow regulating valve means being spring biassed towards a closed position and capable of being depressed towards an open position by means of a force which acts on an actuator means and which is greater than the force represented by the spring bias.

One such sample taking device is known from U.S. Pat. No. 4,326,541. This known sampling device affords several important advantages in comparison with the technique most often used in health care when taking venous samples of body fluid. The standard sample taking device in current use includes a carrier which supports two puncture needles. The needles project from the carrier in two mutually opposite directions and are in direct communication with each other. When using this known device, one of the needles is inserted into a vein or like blood vessel and a stoppered vacuum-type test tube is then pushed axially onto the other needle. When the needle has penetrated the stopper, the desired amount of blood is drawn from the vein into the tube through the medium of the partial vacuum prevailing therein.

One drawback with this known method is that the vacuum tube cannot be pushed onto its associated needle until the other needle has been inserted into a vein, or like blood vessel, since otherwise the partial vacuum in the tube would be equalized and no suction would be obtained when subsequently attempting to take a sample. Furthermore, a certain amount of force is required to fit the test tube to the rear needle when the front needle is inserted, and consequently there is a danger that the front needle will be pushed further into the vein and possibly out through the opposite wall thereof, which puts the patient at serious risk. In addition, the small needle movements which are inevitable when fitting the vacuum tube to an inserted needle may be painful to the patient.

Another drawback with this known device is that when several tubes are to be filled with sample liquid sequentially from one and the same vein, sample liquid is liable to spill during the interchange of tubes. To overcome this, the rear needle, which is intended to pierce the sealing stoppers of respective tubes, is fitted with a check valve in the form of a rubber hose. The seal afforded by this valve, however, is impaired by the repeated puncturing of consecutive stoppers, with the subsequent risk of sample fluid escaping to the surroundings. This escape of fluid constitutes a serious problem with respect to the risk of spreading infection.

These problems are solved by means of the fluid sampling device described in the aforesaid U.S. Pat. No. 4,326,541. This known device includes a flow regulator which normally blocks the passageway between the two needles and which when in a closed position prevents the partial vacuum prevailing in a vacuum tube from being equalized, thereby enabling the vacuum tube to be fitted onto one needle before inserting the other needle into a vein or like vessel. Thus, a vein can be punctured with a vacuum tube attached to the rear needle, thereby obviating the need to fit the vacuum tube at a later stage and therewith avoiding the risk of transection of the vein and also of causing the front needle to move subsequent to its insertion. This risk is also reduced still further by the fact that the force required to operate the check valve acts perpendicularly to the longitudinal axes of the needles, and not in the direction of said axes. Another advantage afforded by this known device is that communication between respective needles can be interrupted with the aid of the flow regulator when changing vacuum tubes, therewith eliminating the risk of spillage.

This known sampling device, however, is also encumbered with a number of serious drawbacks. For example, when the device is at rest the flow passageway through the two needles is closed, which means that it will also be closed when the device is sterilized prior to being used, which is highly disadvantageous. Furthermore, since the resilient valve body of the flow regulator is normally in contact with precisely the same orifice-defining surfaces of respective needles when the valve is closed, the valve body is likely to suffer wear and fatigue when the device is stored inactive for long periods, therewith increasing the risk of leakage. When leakage occurs, the vacuum conditions in the tube are broken before the front needle can be inserted into a vein, therewith making it difficult or impossible to take a sample.

A further disadvantage with this known sampling device is that it lacks a separate cover for the front needle. In the case of conventional needle covers which solely surround the needle itself, the opening through which the needle is inserted into the cover is so small that the user runs the risk of pricking him- or herself by the needle. This is extremely hazardous from the aspect of infection.

The main object of the present invention is to provide fluid sampling equipment of the kind mentioned in the introduction with which at least the drawbacks of the known sampling device are overcome. This object is achieved in that the equipment also includes a protective cover or casing which serves the dual purpose of protecting the front needle and of enabling the passageway between the two needles to be kept open in the rest position of the sampling device, which according to the aforegoing is highly beneficial when sterilizing the sampling device and which will also reduce the risk of leakage due to fatigue of the valve material. The sampling equipment, however, shall be constructed so that the flow regulator closes the passageway through the needles quickly and effectively immediately upon withdrawal of the sampling device from the protective cover, thereby enabling a vacuum tube to be fitted without risk of the vacuum conditions being broken.

The inventive sampling equipment is particularly characterized in that it includes a protective cover which is intended to accommodate the sampling device and which comprises a part which protects the front needle and a part which exerts on the actuator means a force such as to hold the flow regulator pressed inwardly and the flow passageway through the needles open when the sampling device is housed in the protective cover.

The protective cover is preferably funnel shaped, to facilitate insertion of the needle point and therewith reduce the risk for the user of pricking him or herself by the needle. The protective cover is also preferably joined to locking means in the form of an end cap which is intended to co-operate with the end of the sampling device to which a vacuum tube is fitted. The end cap is preferably joined to the protective cover by means of a connector strip formed integrally with the protective cover. The end cap is also preferably formed integrally with said connector strip and joined thereto via a hinge-forming part thereof.

In accordance with one particularly preferred embodiment of the invention, the front needle is provided with a mounting which is so configured that when fitting the needle to a corresponding fitting means on the sampling device, the needle is positioned so that a bevelled surface on the pointed end of the needle is located at a pre-determined angle relative to said actuator means. The mounting and fitting means of the needle and the sampling device respectively are preferably so configured that the bevelled surface will essentially point towards said actuator means when the needle is fitted to the sampling device.

As a result of this arrangement, the person inserting the needle into a blood vessel of a patient will constantly be aware of the direction in which the bevelled surface of the needle is turned. It is important to know the location of this bevelled surface when piercing a vein or like blood vessel. The person taking the blood sample is also required to inspect the needle for damage both before inserting the needle and subsequent to its withdrawal.

Other characteristic features of the invention are set forth in the following claims.

The invention will now be described in more detail with reference to the accompanying drawings.

Figure 1:
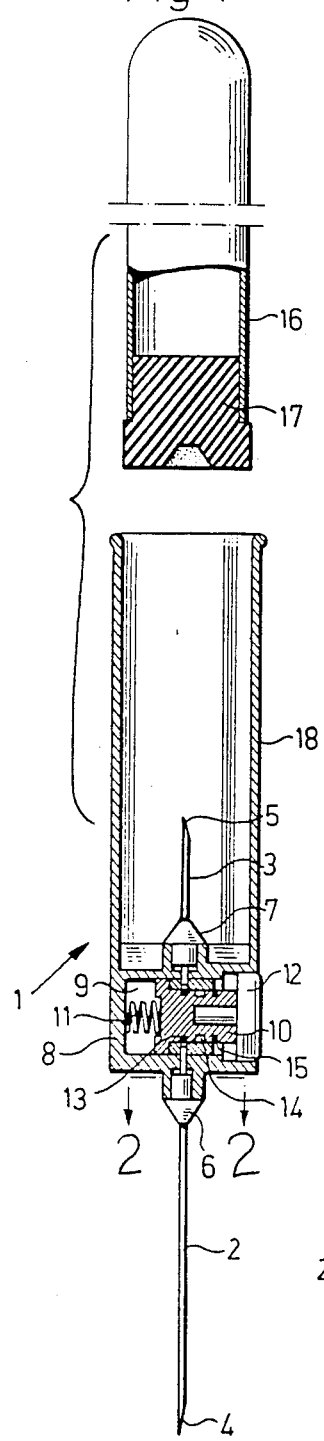
FIG. 1 is a longitudinal sectional view of a sampling device included in the inventive sampling equipment.

In FIG. 1 the reference numeral 1 identifies a sampling device according to the invention which includes two mutually opposed needles 2 and 3, the mutually distal ends of which are bevelled to form respective sharp points 4 and 5. Each of the needles is provided with respective mountings 6 and 7 which fit into respective socket fittings located on a central part 8 of the sampling device. Located within the central part 8 of the sampling device is a space 9 which forms a valve chamber for a flow regulator in the form of a valve slide 10. The slide is connected with an actuator means 12 located on one side of the central part 8 and is arranged to be moved by said actuator means in a direction perpendicular to the longitudinal axes of the needles, against the action of a spring 11.

When the sampling device is at rest, as illustrated in FIG. 1, the mutually opposing ends of the needles 2 and 3 are sealed with the aid of an O-ring 13 extending around the slide 10. When the slide 10 is moved by pressing the actuator means 12, a circumferential groove 14 on the slide 10 is moved into register with the mutually facing orifices of the needles so as to establish a flow passage therebetween. The reference 15 identifies a further O-ring.

The embodiment illustrated in FIG. 1 also includes a vacuum tube 16 which is fitted with a rubber stopper 17 which is pierced by the rear needle 3 when the tube 16 is inserted into a cylindrical hollow carrier 18 formed integrally with the centre part 8 of the sampling device.

Subsequent to inserting the tube 16 into the carrier 18, the sampling device is ready for use. The front needle 2 is then inserted into a vein and the connection between the two needles 2 and 3 is opened, by pressing in the actuator means 12 against the action of the spring 11. The vacuum conditions prevailing in the tube 16 will then cause a quantity of sample fluid to be drawn into the tube. Subsequent to releasing the holding pressure on the actuator means, the tube can be withdrawn from the tube carrier 18 and replaced with a fresh vacuum tube, if further quantities of sample are required. Since the passageway between the two needles is closed during this tube interchange, no sample will be spilled during the course of changing the tubes.

Figure 2:
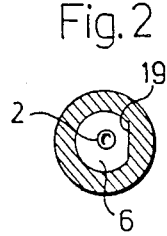
FIG. 2 is a cross-sectional view taken on the line II—II in FIG. 1.

As will be seen from FIG. 2, the mounting 6 on the front needle 2 has a flat surface 19, which co-acts with a corresponding surface on the socket-like fitting on the sample taking device. These mutually co-acting surfaces ensure that the bevelled surface on the point 4 of the front needle 2 will be located constantly at a given angle in relation to a plane passing through the actuator means 12 and preferably pointing in the direction of the external surface thereof as in the illustrated case, such that the person taking a blood sample will always know the direction in which the bevelled surface points. This is highly beneficial when actually inserting the needle into a vein or like vessel and when examining the point of the needle before and after inserting said needle.

Figure 3:
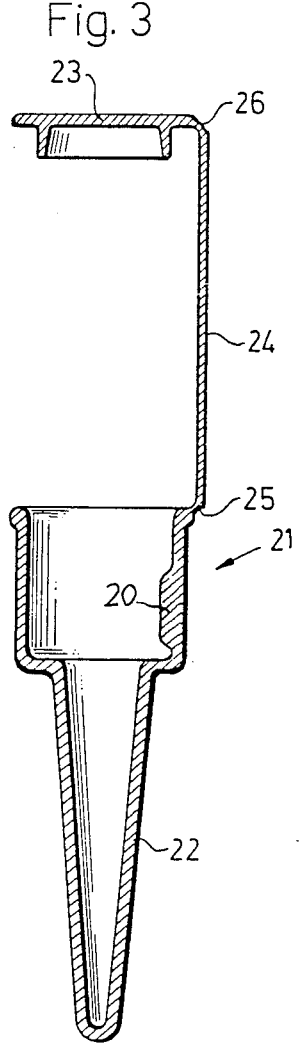
FIG. 3 is a longitudinal sectional view of a protective cover intended for the sampling device of FIG. 1 and forming part of the inventive equipment.
Figure 4:
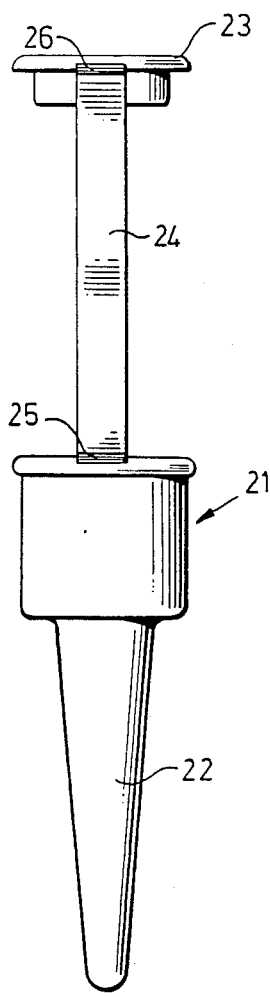
FIG. 4 is a side view of the protective cover illustrated in FIG. 3.

FIGS. 3 and 4 illustrate a protective cover which is intended for the illustrated sample taking device. The illustrated protective cover comprises a part 22 which covers and protects the front needle 2 and which has a funnel-like configuration so as to facilitate insertion of the needle into said cover part and therewith reduce the risk for the user of pricking him- or herself by the needle. The reference 23 identifies an end cap which is configured for co-action with the open end of the tube carrier in a manner to secure the sampling device in the protective cover 21. The end cap 23 is joined to the part 22 of the protective cover 21 by means of a connecting strip 24. The whole of the protective cover 21 according to the illustrated embodiment, including the connecting strip and the end cap, has the form of a one piece structure fabricated from a plastics material and incorporates hinge-like weakened portions 25 and 26 at respective junctures between the funnel-shaped part 22 and the connecting strip 24 and between the connecting strip and the end cap 23.

Figure 5:
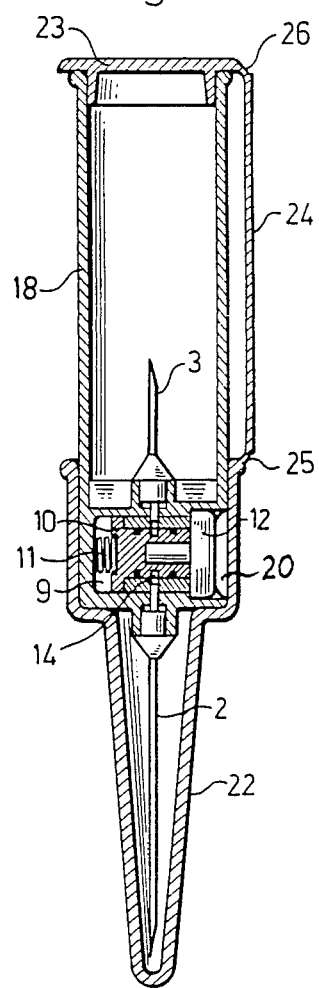
FIG. 5 is a longitudinal sectional view of the full set of equipment according to the invention.

FIG. 5 is an illustration which shows the sampling device of FIG. 1 inserted into and securely held in a protective cover according to FIGS. 3 and 4. It will be seen from FIGS. 3 and 5 that the upper portion of the funnel-shaped part 22 of the protective cover includes a projecting part or button 20 designed to exert on the actuator means, when in position on the sampling device, a force which presses in the actuator means 12 to a position in which communication is established between the needles and holds the same depressed. Thus, the passageway between the two needles 2 and 3 is open when the sampling device is housed in its protective cover, in storage, which according to the aforegoing affords important advantages, insomuch that the sampling device can be sterilized more efficiently and that the rubber seal 13, which is intended to hold the connection between the two needles closed prior to taking a sample, is less likely to become worn or fatigued.

The actuator means 12 is released as soon as the end cap 23 is lifted and the sampling device is removed from the protective cover, whereby the spring 11 returns the valve slide 10 to its rest position in which open communication between the two needles is broken. With the valve plate in this position a vacuum tube 16 can be inserted safely into the carrier 18, as described with reference to FIG. 1, while ensuring that the rear needle 3 pierces the rubber stopper 17 of the tube. The sampling device is now ready for immediate use. The person taking the sample is aware of the orientation of the bevelled surface of the needle end 4 from the instant location of the actuator means 12, and can thus ensure that the vein is pierced with said bevelled surface facing in the correct direction.

Although the above description has been made with reference to one embodiment of sample taking equipment according to the invention, it will be understood that various modifications can be made within the scope of the following claims. For example, the control part 8 of the sampling device and the flow regulator may have forms different to those of the illustrated embodiment. The manner in which the actuator means 12 co-acts with the protective cover to open the passageway between the needles may also be different to that described, the only requisite being that the passageway through the needles is held open until the sampling device is removed from the protective cover. The protective cover and the end cap may also take different forms to those illustrated, while retaining their intended function.

I claim:

1. Equipment suited for taking fluid samples from patients and comprising a sample taking device (1) having in mutually opposed relationship a front needle (2) and a rear needle (3), the pointed ends (4, 5) of which are turned away from one another and of which needles the pointed end (4) of the front needle (2) is intended to perforate a vein or like blood vessel, and the pointed end (5) of the rear needle (3) is intended to penetrate a sealing stopper (17) of a vacuum-type test tube (16) capable of being inserted partially into the sample taking device, and which sample taking device (1) further comprises a flow regulator (10) which is arranged in a space (9) located between the mutually opposite ends of respective needles and intended for regulating the flow of fluid through the needles, said flow regulator being-spring biassed towards a closed position and capable of being pressed in towards an open position by a force capable of overcoming the spring bias and created through the medium of an actuator means (12), wherein the sample taking equipment also includes a protective cover (21) which is intended to accommodate the sample taking device (1) and which has a part (22) which protects the pointed end (4) of the front needle and a part (20) which exerts on the actuator means (12) a force such as to hold the flow regulator (10) pressed in and the flow passageway through the needles (2, 3) open when the sample taking device (1) is introduced into the protective cover (21).

2. Equipment according to claim 1, wherein the protective cover (21) has a funnel-like shape, such as to facilitate insertion of the pointed end (4) of the needle into the protective cover and therewith reduce the risk of damage to said pointed end.

3. Equipment according to claims 1 or 2, wherein the protective cover (21) has connected thereto a securing means in the form of an end cap (23) which is intended to co-act with the end of the sample taking device (1) intended to receive a test tube (16).

4. Equipment according to claim 3 wherein the end cap (23) is joined to the protective cover (21) by means of a connecting strip (24) formed integrally with the protective cover.

5. Equipment according to claim 4 wherein the end cap (23) is formed integrally with said connecting strip (24) and is joined therewith through a hinge-like part (26) of the protective cover.

6. Equipment according to of claim 1 or 2, wherein the front needle (2) is provided with a mounting (6) so configured that when fitted to a corresponding socket-like fitting on the sample taking device (1) the needle (2) is automatically brought to a position in which a bevelled surface on the pointed end (4) of said needle is located at a pre-determined angle in relation to said actuator means (12).

7. Equipment according to claim 6, wherein said mounting (6) and said socket-like fitting are configured so that the bevelled surface of the needle (2) points substantially in the direction of the outer surface of said actuator means (12).

8. Equipment according to claim 1, wherein said flow regulator includes a valve slide (10) which can be displaced in the direction of its longitudinal axis in said space (9) and which is provided with a flow passage (14) which in the inwardly pressed position of the slide establishes an open connection between the two mutually opposite ends of the two needles (2, 3).

9. Equipment according to claim 8, wherein said flow passage is formed by a groove (14) extending circumferentially around the valve slide.

10. Equipment according to claim 8 or 9, wherein the valve slide (10) is provided with a circumferentially extending O-ring (13) which in the rest position of the slide rests sealingly against the mutually facing ends of the two needles (2, 3).

* * * * *